(12) United States Patent
Menon et al.

(10) Patent No.: US 11,311,250 B2
(45) Date of Patent: Apr. 26, 2022

(54) SPECTROSCOPIC MONITORING FOR THE MEASUREMENT OF MULTIPLE PHYSIOLOGICAL PARAMETERS

(71) Applicant: AMRITA VISHWA VIDYAPEETHAM, Kollam (IN)

(72) Inventors: Unni Krishna K. A. Menon, Kollam (IN); Sruthi Krishna, Kollam (IN); Kripesh V. Edayillam, Kollam (IN); Gayathri Bindu, Kollam (IN); Harikrishnan Krishnannair, Kollam (IN); Maneesha Vinodhini Ramesh, Kollam (IN)

(73) Assignee: Amrita Vishwa Vidyapeetham

( * ) Notice: Subject to any disclaimer, the term of this patent is extended or adjusted under 35 U.S.C. 154(b) by 228 days.

(21) Appl. No.: 16/229,579

(22) Filed: Dec. 21, 2018

(65) Prior Publication Data
US 2019/0192085 A1    Jun. 27, 2019

(51) Int. Cl.
*A61B 5/0205*    (2006.01)
*A61B 5/1455*    (2006.01)
(Continued)

(52) U.S. Cl.
CPC ............ *A61B 5/746* (2013.01); *A61B 5/0075* (2013.01); *A61B 5/02433* (2013.01); *A61B 5/14551* (2013.01); *A61B 5/14552* (2013.01); *A61B 5/14557* (2013.01); *A61B 5/6801* (2013.01); *A61B 5/681* (2013.01); *A61B 5/726* (2013.01);
(Continued)

(58) Field of Classification Search
CPC ..... A61B 5/0205; A61B 5/021; A61B 5/1455; A61B 5/14551; A61B 5/14552; A61B 5/02416; A61B 5/72; A61B 5/7235; A61B 5/7264; A61B 5/726; A61B 5/725; A61B 5/746; A61B 5/6801; A61B 5/681
See application file for complete search history.

(56) References Cited

U.S. PATENT DOCUMENTS

5,431,170 A *  7/1995  Mathews ............... A61B 5/681
                                            600/323
6,893,396 B2 * 5/2005  Schulze ............... A61B 5/0022
                                            600/300
(Continued)

*Primary Examiner* — Eric F Winakur
(74) *Attorney, Agent, or Firm* — Donald R. Boys; Central Coast Patent Agency LLC (57) ABSTRACT

The present disclosure relates to devices, systems, methods and computer program products for continuously monitoring, diagnosing and providing treatment assistance to patients using sensor devices, location-sensitive and power-sensitive communication systems, analytical engines, and remote systems. The method of non-invasively measuring multiple physiological parameters in a patient includes collecting photoplethysmograph (PPG) signal data from a wearable sensor device, applying one or more filters to correct the signal data and extracting a plurality of features from the corrected data to determine values for blood glucose, blood pressure, SpO2, respiration rate, and pulse rate of the patient. An alert may be automatically sent to one or more computing devices when the value falls outside a custom computed threshold range for the patient. The method offers ease of usage, allows continuous real-time monitoring of the patient in any setting for timely intervention, and results in improved accuracy of the signal data.

4 Claims, 9 Drawing Sheets

(51) Int. Cl.
*A61B 5/00* (2006.01)
*G16H 40/63* (2018.01)
*G16H 50/30* (2018.01)
*G06N 20/00* (2019.01)
*A61B 5/024* (2006.01)
*A61B 5/08* (2006.01)
*A61B 5/021* (2006.01)
*A61B 5/145* (2006.01)

(52) U.S. Cl.
CPC ............. G06N 20/00 (2019.01); G16H 40/63 (2018.01); G16H 50/30 (2018.01); *A61B 5/0022* (2013.01); *A61B 5/021* (2013.01); *A61B 5/0205* (2013.01); *A61B 5/02116* (2013.01); *A61B 5/02416* (2013.01); *A61B 5/02427* (2013.01); *A61B 5/0816* (2013.01); *A61B 5/14532* (2013.01); *A61B 5/725* (2013.01); *A61B 5/7207* (2013.01); *A61B 5/7264* (2013.01); *A61B 5/7267* (2013.01)

(56) References Cited

U.S. PATENT DOCUMENTS

| | | | |
|---|---|---|---|
| 10,646,144 B2* | 5/2020 | Lamego | A61B 5/14552 |
| 10,799,802 B2* | 10/2020 | Nielsen | A63F 13/42 |
| 10,952,638 B2* | 3/2021 | Lange | A61B 5/14551 |
| 2011/0230744 A1* | 9/2011 | Ribas Ripoll | A61B 5/1455 |
| | | | 600/365 |
| 2013/0261468 A1 | 10/2013 | Semler et al. | |
| 2013/0267796 A1* | 10/2013 | Enric Monte Moreno | |
| | | | A61B 5/14551 |
| | | | 600/301 |
| 2016/0058308 A1* | 3/2016 | Robinson | A61B 5/7275 |
| | | | 600/479 |
| 2018/0090229 A1 | 3/2018 | Sanyal et al. | |

* cited by examiner

SPECTROSCOPIC MONITORING FOR THE MEASUREMENT OF MULTIPLE PHYSIOLOGICAL PARAMETERS

CROSS-REFERENCES TO RELATED APPLICATIONS

The present application claims priority to Indian Patent Application No. 201741046721 filed on Dec. 18, 2018 entitled "SPECTROSCOPIC MONITORING FOR THE MEASUREMENT OF MULTIPLE PHYSIOLOGICAL PARAMETERS", which claims priority to Indian Provisional Patent Application No. 201741046721 entitled "PHYSIOLOGICAL MONITORING SYSTEM FOR THE MEASUREMENT OF MULTIPLE PARAMETERS" filed on Dec. 26, 2017, both of which are incorporated herein by reference in its entirety.

FIELD OF THE INVENTION

The invention generally relates to health monitoring of patients, and more specifically, to devices, systems and methods to remotely monitor, diagnose and provide treatment assistance.

DESCRIPTION OF RELATED ART

Progress in science and technology have led to the development of high performance monitoring systems with features such as low cost, smaller size, high efficiency, high accuracy, etc. The design and development of Remote Patient Monitoring System (RPMS) to improve quality of human life, especially in rural areas is of particular interest. RPMS not only measures the physiological parameters, but also transmits the data in real time to healthcare professionals wirelessly. This system is extremely useful for getting accurate and reliable information about body parameters and providing rapid access to health information. Wearable RPMS includes many wearable sensors that measure the physiological parameters namely Blood Pressure, Blood Glucose, Blood Oxygen level (SpO2), Pulse Rate, Body Temperatures continuously. The measured physiological data are processed using microcontroller and sent to a doctor's smartphone wirelessly for better health monitoring and analysis. In order to avoid difficulties associated with monitoring parameters using conventional methods, non-invasive methods are taken into account.

There are many technologies available to measure physiological parameters. photoplethysmography (PPG) based technology is one among these methods that is based on optical techniques. Blood volume changes in the arteries produce a proportional change in the light intensity transmitted or reflected through the very sensitive area of the body, such as fingertip, tongue, ear lobe etc. A PPG signal is obtained by passing an LED light through the body tissue. Current research is going on the multi parameter monitoring system using Light Emitting Diode (LED) sensors such as Red, Infra-Red (IR), Green, and photo diodes. Recent advances in optical technology have stepped up the use of high intensity green LED's for PPG sensors. The blood absorbs green lights better than red, IR light sources and it penetrates deeply into tissues. Sensors are fundamental elements of the RPMS which are designed to measure the body parameters accurately and reliably over a long duration.

The US application 20180090229A1 discloses a wearable health monitoring system with a central sensor that receives and processes the measured data from multiple sensors where, each sensor which collects batches of data indicative of one or more physiological parameters of the user at a physiological parameter-specific frequency, for a pre-defined time window. Examples of measurement technologies used include photoplethysmography (PPG), electrocardiography (ECG), 3-axis accelerometry, temperature measurement using thermistors, and electrodermal activity monitoring. Some of the sensors are used primarily or solely to provide calibration signals for other sensors.

The device in the application US20130261468A1 utilizes a non-invasive photo-plethysmographic (PPG) finger- or toe-probe with an infrared transceiver to measure blood perfusion or circulation in an extremity. The described device obtains optical density measurements by intermittently providing a current pulse of known amplitude to the IR emitter, which sends IR light through a patient's body tissue, typically a finger or toe. Such perfusion data is processed using correlation techniques to detect patient hydration.

To achieve the benefits of wearable and continuous monitoring, the sensors should be preferably small in size, low weight, fabricated using low cost materials and be able to transmit data through wireless technologies. The battery life of the sensors and associated systems should be long for effective usage over long duration. Further, the optimized RPMS systems using wearable sensors and wireless communication systems should be able to provide improvement in the quality of human life in remote locations by timely detection and intervention. The present invention thus aims to enhance the wearable device by further miniaturization and improved computational techniques to achieve consumer/clinical grade compliance for multiple parameters, and augment IoT capabilities for efficient and timely communication to remote doctors.

SUMMARY OF THE INVENTION

The invention in its various aspects includes devices, systems, methods and computer readable media for continuously monitoring, diagnosing and providing treatment assistance to patients. In various aspects the method includes using sensor devices, location-sensitive and power-sensitive communication systems and analytic modules.

In one embodiment, a computer-implemented method of non-invasively measuring multiple physiological parameters for health monitoring is disclosed. In the first step, sensor data including photoplethysmograph (PPG) signal data is received by a local computing device or a remote computing device from a wearable sensor device attached to a patient's body. In the next step, one or more filters are applied to remove motion artifacts, noise related interferences, effects of shivering, applied pressure, horizontal or vertical movements associated with the received sensor data. In the next step, a plurality of features including at least systolic duration, diastolic duration, systolic slope, diastolic slope, pulse duration, overall mean, peak amplitude, left half and right half are extracted from the PPG signal data. In the next step, values for blood glucose, blood pressure, SpO2, respiration rate, pulse rate, or a combination thereof are determined from the extracted plurality of features. In the next step, an alert is sent to one or more computing devices when the values for blood glucose, blood pressure, SpO2, respiration rate, pulse rate, or a combination thereof, falls within or above a computed threshold range for the patient. The threshold range computed by a classifier associated with the remote computing device based on historical PPG signal data of the patient and at least one or more additional features including age, gender and disease status of the patient.

In some embodiments, the alert is a moderate alert for the values with the computed threshold. In some embodiments, the alert is a severe alert for values above the computed threshold. In some embodiments, the removal of motion artifacts from the PPG signal may be achieved using low pass butterworth filtering, wavelet transform and thresholding. In some embodiments, the threshold range is computed by a machine learning module trained to detect anomalies based on multiple factors. In some embodiments, the external interferences on the PPG signal is corrected using one or more additional sensors present in the wearable device or the local computing device. In some embodiments, the alert may include a summary of the patient's physiological parameters. In some embodiments, the accuracy of the determined values is greater than 90% for pulse rate, greater than 90% for SpO2, greater than 80% for blood pressure, and greater than 70% for blood glucose. In some embodiments, the one or more additional features are extracted from a hospital information system (HIS). In some embodiments, the threshold range for the patient is computed further based on one or more additional sensors present in the wearable device or the local computing device.

In one embodiment, a non-invasive remote health monitoring system for measuring multiple physiological parameters is disclosed. The system includes one or more processing units and one or more memory units coupled to the one or more processing units. The memory unit includes a signal analytics module configured to receive sensor data of a patient from a wearable sensor device. The sensor data includes at least photoplethysmograph (PPG) signal data. The signal analytics module is further configured to apply one or more filters to remove motion artifacts, noise related interferences, effects of shivering, applied pressure, horizontal or vertical movements associated with the received sensor data, and extract a plurality of features from the PPG signal data. The plurality of features includes at least systolic duration, diastolic duration, systolic slope, diastolic slope, pulse duration, overall mean, peak amplitude, left half and right half. The signal analytics module is further configured to determine values for blood glucose, blood pressure, SpO2, respiration rate, pulse rate, or a combination thereof, from the extracted plurality of features. The system further includes a machine learning module configured to compute a threshold range for the patient based on historical PPG signal data of the patient and at least one or more additional features including age, gender and disease status of the patient. The system further includes an alert module configured to send an alert to one or more computing devices when the values for blood glucose, blood pressure, SpO2, respiration rate, pulse rate, or a combination thereof, falls within or above the computed threshold range for the patient. The system further includes a summarization module configured to display a summary of the patient health status on the one or more computing device.

In one embodiment, a wearable, non-invasive, health-monitoring IoT device for use in the method or system is disclosed. The device includes an optical sensor unit including a LED source coupled to a photodetector. The optical sensor unit is configured to obtain photo-plethysmograph (PPG) signal data from a patient's body using near infrared (NIR) spectroscopy. The LED source includes at least a red LED source configured to be detected by the photodetector at 660 nm and an infrared (IR) LED source configured to be detected by the photodetector at 910 nm. The device further includes an analog front end (AFE) unit configured to convert the received PPG signal data to digital signal data. The device further includes a power source and a microcontroller configured to wirelessly transmit the digital signal data to a computing device for determining physiological parameters of the patient. In some embodiments, the alert is a moderate alert for the values with the computed threshold. In some embodiments, the alert is a severe alert for values above the computed threshold.

In various embodiments, a non-transitory machine-readable storage medium storing instructions which, when executed by one or more processors, cause the one or more processors to perform operations is included.

This and other aspects are disclosed.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The various architectural components of the present invention may be distributed across various special purpose or general purpose computing devices, including various hardware components, such as personal computers, servers, laptops, hand-held devices, cell phones or the like, as discussed in greater detail below. Some or all of the components may comprise or reside on separate computing devices or on the same computing device.

The term "computing device" encompasses devices such as servers, desktop computers, laptop computers, tablet computers, personal digital assistants (PDA), smartphones, mobile phones, smart devices, appliances, sensors, or the like. The computing devices may include processing units, memory units, video or display interfaces, input/output interfaces, video or audio recording units, buses that connect the various units, network interfaces, peripheral interfaces, and the like. It may include any client device or a series thereof that may perform the desired computing operation and may include "rich" devices that are capable of performing a high degree of data processing such as desktop personal computers (PCs) and "thin" clients that are less capable of processing data such as cellular phones and pagers. It is understood that the distinction between a rich client and a thin client is a spectrum; there are many devices (hand-held or Tablet PCs) for example, that fall in the middle of the spectrum. Regardless of the device type or the processing capability of the client, most client devices may be operated by a user in either an online or offline state.

The terms "mobile device", "smart device", "cellular device", and "wireless device" may be used interchangeably and refer to any one of the various cellular telephones, smart phones, multimedia enabled cellular telephones and similar electronic devices capable of sending and receiving wireless communication signals. In an embodiment, the wireless device is a cellular handheld device (e.g., a mobile device), which can communicate via a cellular telephone communication network. The terms "app", "application", "program", and "software" may be used interchangeably and may include standalone applications, SDKs, and modules of applications or operating systems.

The devices may be configured to utilize various communication protocols, such as Global System for Mobile Communications (GSM), General Packet Radio Services (GPRS), Enhanced Data GSM Environment (EDGE), Code Division Multiple Access (CDMA), Wideband Code Division Multiple Access (WCDMA), Bluetooth, High Speed Packet Access (HSPA), Long Term Evolution (LTE), 5G, 5G-New Radio, and Worldwide Interoperability for Microwave Access (WiMAX).

Embodiments within the scope of the present invention also include computer-readable media for carrying or having computer-executable instructions or data structures stored thereon. Such computer-readable media can be any available media which can be accessed by a general purpose or special purpose computing device. By way of example, and not limitation, such computer-readable media can be physical storage media such as RAM, ROM, EEPROM, CD-ROM or other optical disk storage, non-volatile storage, magnetic disk storage or other magnetic storage devices, or any other medium which can be used to carry or store desired program code means in the form of computer-executable instructions or data structures and which can be accessed by a general purpose or special purpose computing device. When information is transferred or provided over a network or another communications connection (either hardwired, wireless, or a combination of hardwired or wireless) to a computing device, the computing device properly views the connection as a computer-readable medium. Thus, any such a connection is properly termed a computer-readable medium. Combinations of the above should also be included within the scope of computer-readable media. Computer-executable instructions comprise, for example, instructions and data which cause any general or special purpose computing device to perform a certain function or group of functions.

The invention in its various embodiments discloses devices, systems, methods and computer program products for continuously monitoring, predicting, diagnosing and/or providing treatment assistance to patients. The system may include sensor devices, location-sensitive and power-sensitive communication systems and analytics platform. In one embodiment, an IoT enabled wearable sensor device for use in remote monitoring of a patient is provided. The device is configured to measure multiple physiological parameters of a patient using NIR spectroscopy and transmits the sensed data signal from the sensors to systems and/or sub-systems for further analysis. In another embodiment, the invention relates to a method of non-invasively measuring multiple physiological parameters using near infrared (NIR) spectroscopy. The data signal bearing the patients parameter is received by a computing device which processes the signals with the help of a server and machine learning models to obtain the patient's measured physiological parameters from the signal and displayed on the device. In yet another aspect, the invention relates to a remote health monitoring system for monitoring and tracking of patient health status even in sparsely connected rural and remote regions.

Figure 1:
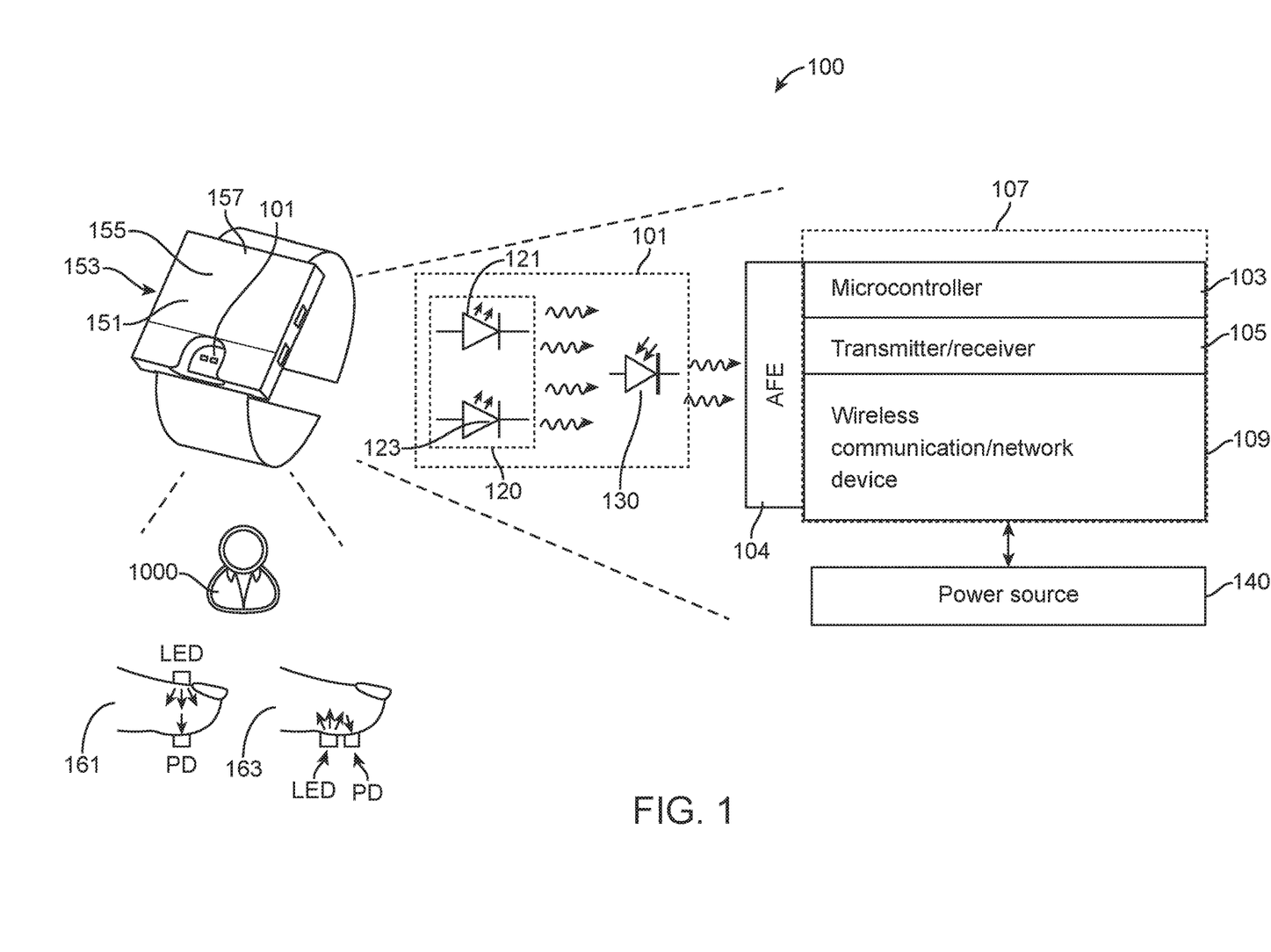
FIG. 1 shows a wearable, non-invasive IoT device.

Referring now to FIG. 1, a non-invasive IoT (Internet of things)-based device 100 for use in health monitoring systems and methods is illustrated, according to one embodiment of the invention. The device 100 may be a wearable device, which can be attached to any part of the body of a user 1000, such as the hand/wrist of the user, typically a thin part of the user's body, more typically a finger, nasal septum, cheek, tongue, toe, or earlobe of a user. The device may be fabricated in in any wearable form, typically a miniaturized form such as a watch, ear piece, ring, and fingertip attachment. The device 100 includes a single optical sensor 101 coupled to an analog front end (AFE) unit 104 and a microcontroller unit 107. The microcontroller unit 107 may include at least a microcontroller 103, a transmitter-receiver unit 105 and a wireless communication unit 109. The optical sensor 101 includes a LED source 120 coupled to the photodetector 130. In a typical embodiment, the LED source 120 includes a combination of a red LED 121 and a IR LED 123, more typically a plurality of red LEDs (121-1, . . . 121-n) and a plurality of IR LEDs (123-1, . . . 123-n). In a typical embodiment, the red LEDs are detectable at a wavelength of about 660 nm. In a typical embodiment, the IR LEDs are detectable at a wavelength of about 910 nm. The photodetector 130 may include one or more photodiodes. The coupling of the LED source and the one or more photodiodes is achieved by positioning the pair suitably, such as by placing them opposite to each other, adjacent to each other, or at an angle. It further includes a power source 140, such as a rechargeable battery unit coupled to the microcontroller unit 107. In some embodiments, the device 100 further includes one or more additional sensor units, such as an accelerometer 151, a temperature sensor 153, a barometric pressure sensor 155 and a gyrometer 157. The device components may be in any suitable form factor known in the art.

The device 100 measures physiological signals for various parameters using near infrared (NIR) spectroscopy technique. The positioning of the photodiode(s) and LEDs allows non-invasive measurements of multiple physiological signals by photoplethysmography (PPG) technique from the user's body, typically through a finger or skin surface on which the device is fitted and acts as measurement sites. The PPG signal, measured as intensity variation in reflected or transmitted light emitted by the LEDs, may be obtained by any suitable mode known in the art such as transmission PPG 161 or reflectance PPG 163. The physiological parameters may include vitals such as blood glucose (BG), blood pressure (BP), blood oxygen level (Spo2), pulse rate and respiration rate. The LEDs emit light signals into the patient's body. The light gets absorbed, reflected and/or scattered by the blood molecules and body tissues. In some embodiments, the difference in wavelengths of reflected red and IR light signals enables sensing of change in blood volume. The difference in intensities of the wavelengths is recorded as PPG signal using the photo detector 130. In some embodiments both the direct current (DC) and alternating current (AC) waveform of the PPG signal data is utilized for determining the parameters such as blood oxygen level (SpO2). One or more such devices may be attached to the user's body at various locations for providing multi-site photoplethymography.

Figure 2:
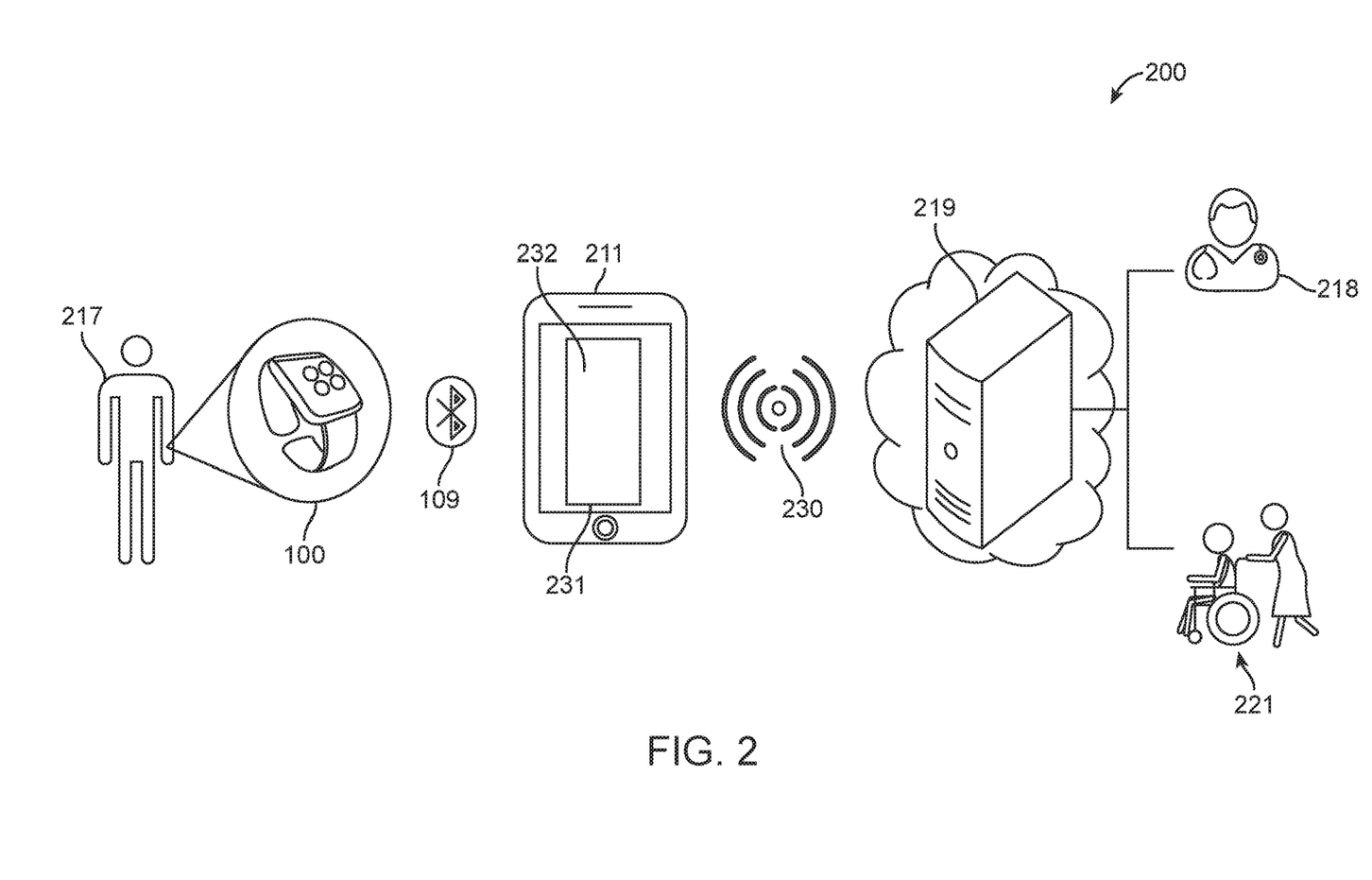
FIG. 2 shows the wearable, non-invasive IoT device coupled to a computing system for monitoring a patient's physiological parameters.

Referring now to FIG. 2, a system for monitoring physiological parameters from the sensor device 100 is illustrated, according to one embodiment of the invention. The detected sensor signal data includes PPG signal data, which is indicative of the physiological data. The sensor data is converted to a digital signal data in the AFE unit 104 and transmitted via a wireless communication unit 109, such as a short-range wireless technology like Bluetooth or the like, for further processing. The device 100 is configured to wirelessly connect to the user's computing device 211, such as a local computing device, smart device or mobile phone, through an application 231 installed in the device 211, as shown in FIG. 2. The device 211 is connected to a remote computing device 219, such as a cloud-based server, through a network 230. The cloud-based server may be further connected to various other systems, such as hospital information systems (HIS) systems interfacing with a health care provider 221, or a clinician/doctor 218. The device 211 may include sensors such an accelerometer, gyrometer, temperature sensor, and barometric pressure sensor. The application 231 provides a graphical user interface 232 which allows a user to interact with the system to obtain immediate feedback on the quality of signals (strength, stability, etc.) generated by the device 100 and/or obtain suggestions for improvement of the signal such as by adjusting their finger, or get into the right posture so as to enable a meaningful signal capture. Further, the user interface allows the user to get crucial details such as network availability, power consumption and battery life of the device.

The signal data obtained from the device 100 is used for continuously monitoring, predicting, diagnosing and/or providing treatment assistance to the user, such as in a remote or out-patient setting as illustrated further below. The miniaturized device is fabricated at a very low cost. Further, the device non-invasively stores, tracks, communicates, and/or analyzes a range of clinically relevant parameters indicative of medical signs of a user and is configured to function at a near real-time. It is suitable for remote usage or out-patient usage, is easily fitted without special training, generates accurate signal data, and can be worn by the user for a long time as it consumes very little power.

Figure 3A:
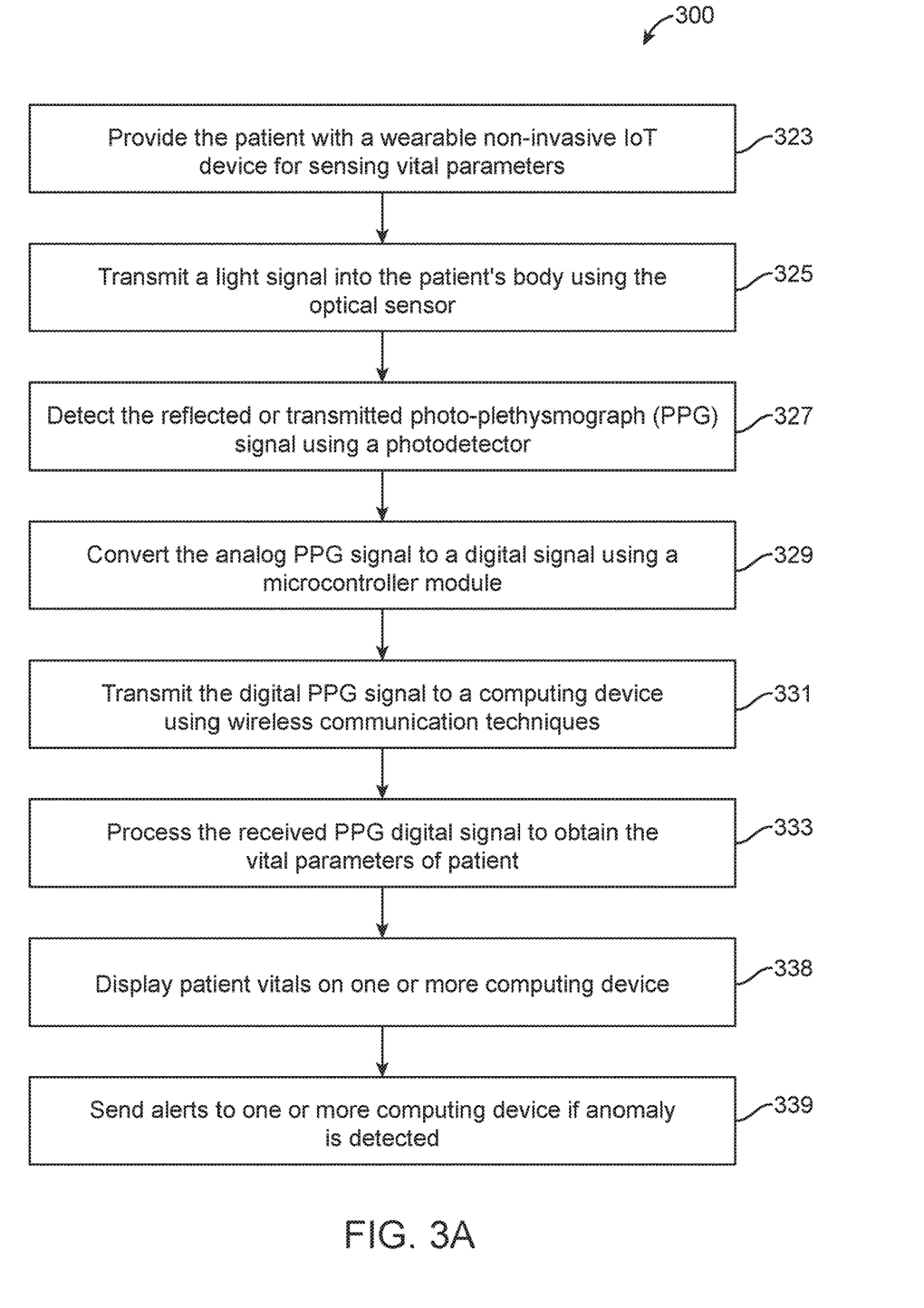
FIG. 3A delineates the steps involved in method of non-invasively measuring multiple physiological parameters using near infrared (NIR) spectroscopy.

A method 300 of monitoring multiple physiological parameters of a patient, non-invasively using near infrared (NIR) spectroscopy technique is delineated in FIG. 3A. The method focuses on the conversion of the PPG signal data sensed from a patient into measured physiological parameters of the patient including BP, BG, SpO2, respiratory rate and pulse rate of a patient. The user is provided with the wearable non-invasive IoT device in block 323. The user may be a known subject or new subject registered with a hospital information system (HIS). The user installs the application 231 in their computing device 211, such as a smart device or cellular phone as a part of the device installation and activation. The user wears the device over a period of time for monitoring the multiple physiological parameters. The device detects PPG signal and converts it to digital signal data in blocks 325, 327, and 329. The PPG signal data transmitted from the wearable sensor device 100 is received by the smart device 211, in block 331. The PPG signal data may be initially processed in the smart device 211 itself and/or sent to a remote computing device 219, such as a server which is connected to other systems for further processing in block 333. The AC and DC components of the combined red and IR light signals may be utilized in determining the vital parameters such as blood oxygen level (SpO2). The predicted patient physiological parameters are displayed on the smart device screen. The patient parametric data is shared with a medical practitioner 218 and/or a care giver 221 for diagnosis and treatment assistance.

Figure 3B:
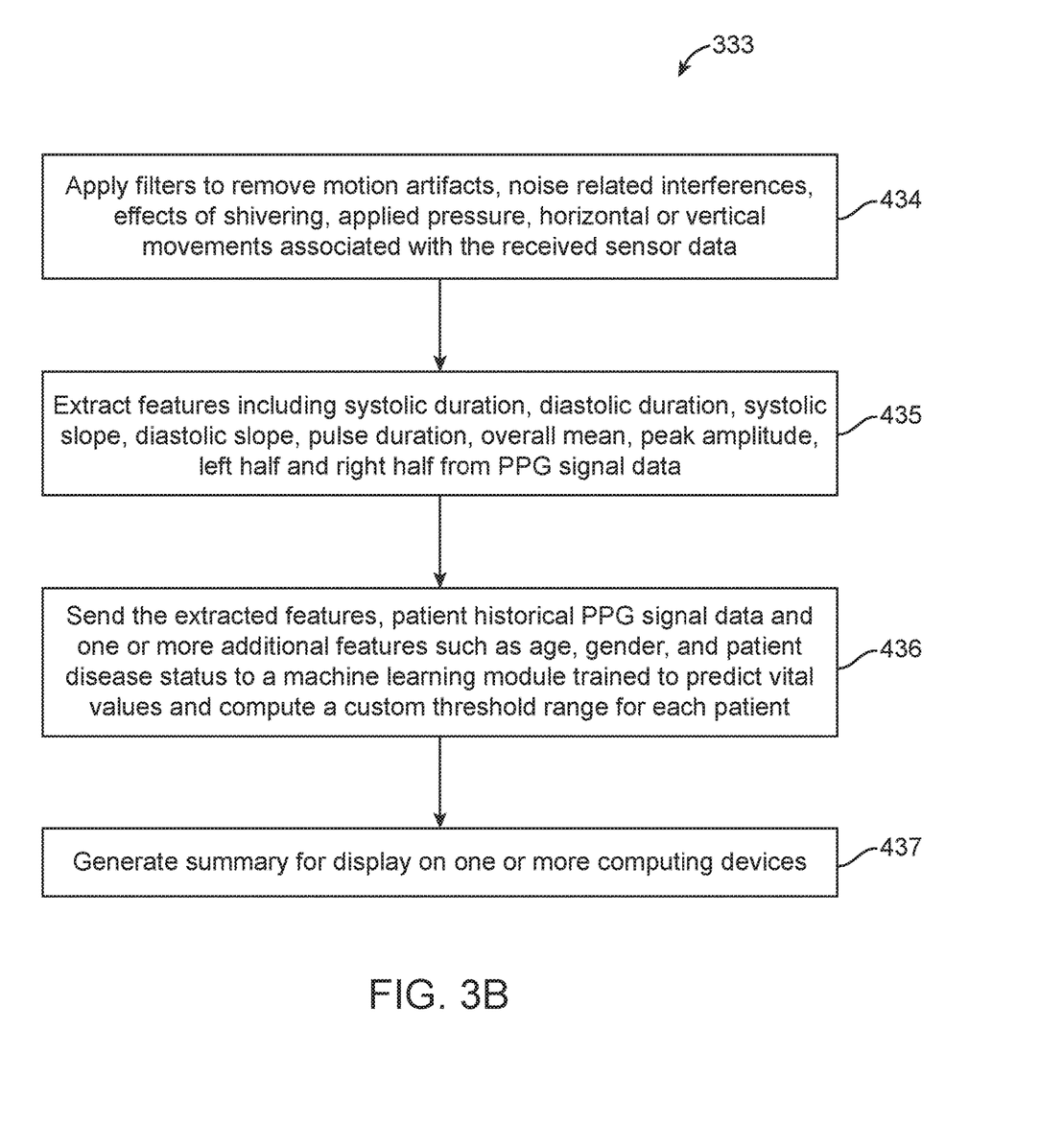
FIG. 3B shows the steps involved in the analysis of PPG signal data.

The processing steps conducted may include signal data filtering and optimization in step 434, signal data extraction in step 435, vital value prediction, and generating a custom threshold range using a machine learning module in step 436, and summary generation in step 437 as depicted in the flowchart in FIG. 3B.

In various embodiments, the data filtering and optimization step 434 may include using various filtering techniques to remove artifacts. In one embodiment, a low pass Butterworth filter and wavelet transform method is used to remove the motion artifacts from the extracted PPG data. The collected PPG data is fed to low pass Butterworth filters followed by application of wavelet transform technique with thresholding at first, second and third levels. In some embodiments in step 435, the signals are extracted by removing the effects of shivering, applied pressure, horizontal and vertical movements and other external interferences on the signal. The step may further involve combining the signal with output from additional sensors present in the wearable device or the local computing device, such as an accelerometer and/or gyrometer, accessed through the application 231 included in the smart device 211.

In some embodiments, the accuracy of the measured physiological parameters may be improved using machine or deep learning techniques in step 436. This step may include applying machine learning algorithms and predictive analytical algorithms to the extracted PPG signal data for correcting deviations and the improvement of accuracy of the physiological parameters. The extracted features from PPG signal data is used as a first level input to the machine learning module. In some embodiments sensor signal data, such as position of patient based on motion tracking, may also be used additionally by the ML module. In some embodiments one or more additional features obtained from other data sources connected to the computing device 211, such as a hospital information system (HIS) which may provide age, gender, and disease status of the patient, may be additionally used by the ML module. A predicted value and custom threshold value is generated for each patient. In various embodiments, the predicted custom threshold value may be based at least in part on a probabilistic model, standard computing measures, and/or features information and attributes. The custom threshold range may be a value or range of values obtained for individual parameter values such as BP, BG, SpO2, respiratory rate, pulse rate or the like, based on an error estimate such as standard deviation or standard error. In other embodiments, the custom threshold range may be a weighted composite value or range based on individual parameters. In some embodiments, various learning algorithms and machines, such as linear support vector regression, linear support vector machines, logistic regression, non-linear regression, inference, decision trees, and naive Bayes may be implemented to train the models for threshold value range identification.

The machine learning (ML) module is trained in step 436 in various embodiments, to detect anomalies based on multiple factors. The training may be done using a training dataset including PPG signal data along with a reference dataset on the server 219, containing standard values of each physiological parameter. In some embodiments, the classifier is trained using a reference dataset containing the physiological parametric data obtained from PPG signal for a large population group. In some embodiments, the reference data is matched to a validation dataset containing values obtained using invasive measurements. In some embodiments, a training dataset, a validation dataset, and a testing dataset may be created based on data collected from data samples. In one embodiment the machine learning model may be tuned using the validation dataset. In one embodiment the performance of the one or more machine learning models may be evaluated using the test dataset.

In various embodiments, the reference and training data sets used by the ML module in step 436 may be specific to the parameter being predicted. In one embodiment, reference data set for the measurement of glucose non-invasively, may include readings from invasive glucose measurements mapped against the features like PPG signal amplitude, or pulse duration. In some embodiments reference data set to derive blood pressure data from fingertip readings may include readings of blood pressure from sphygmomanometer and pulse duration of PPG signal. Similarly, reference pulse oximeter reading against PPG signal from both red and IR LED's may be considered as reference datasets for SpO2 measurement. Similarly, reference datasets for respirational rate and pulse rate from invasive, semi-invasive and traditional techniques may be used for training the ML module. The reference datasets may in various embodiments further include subsets including other variables that may affect the threshold values for the vitals such as pre-existing disease status, state of glucose measurement (fasting, random), motion tracking (sitting, standing, in motion), etc.

In various embodiments, a summary of patient's physiological parameters is sent as a part of the alert in step 437. The alert may evoke different responses depending on its severity. There may be no alert if the values fall below the threshold. In some embodiments, the alert is classified as a moderate alert if it is within a below threshold. In some embodiments, the alert is classified as a severe alert if it is above a certain threshold. In other embodiments, a user receiving the alert can access the report remotely.

Figure 4A:
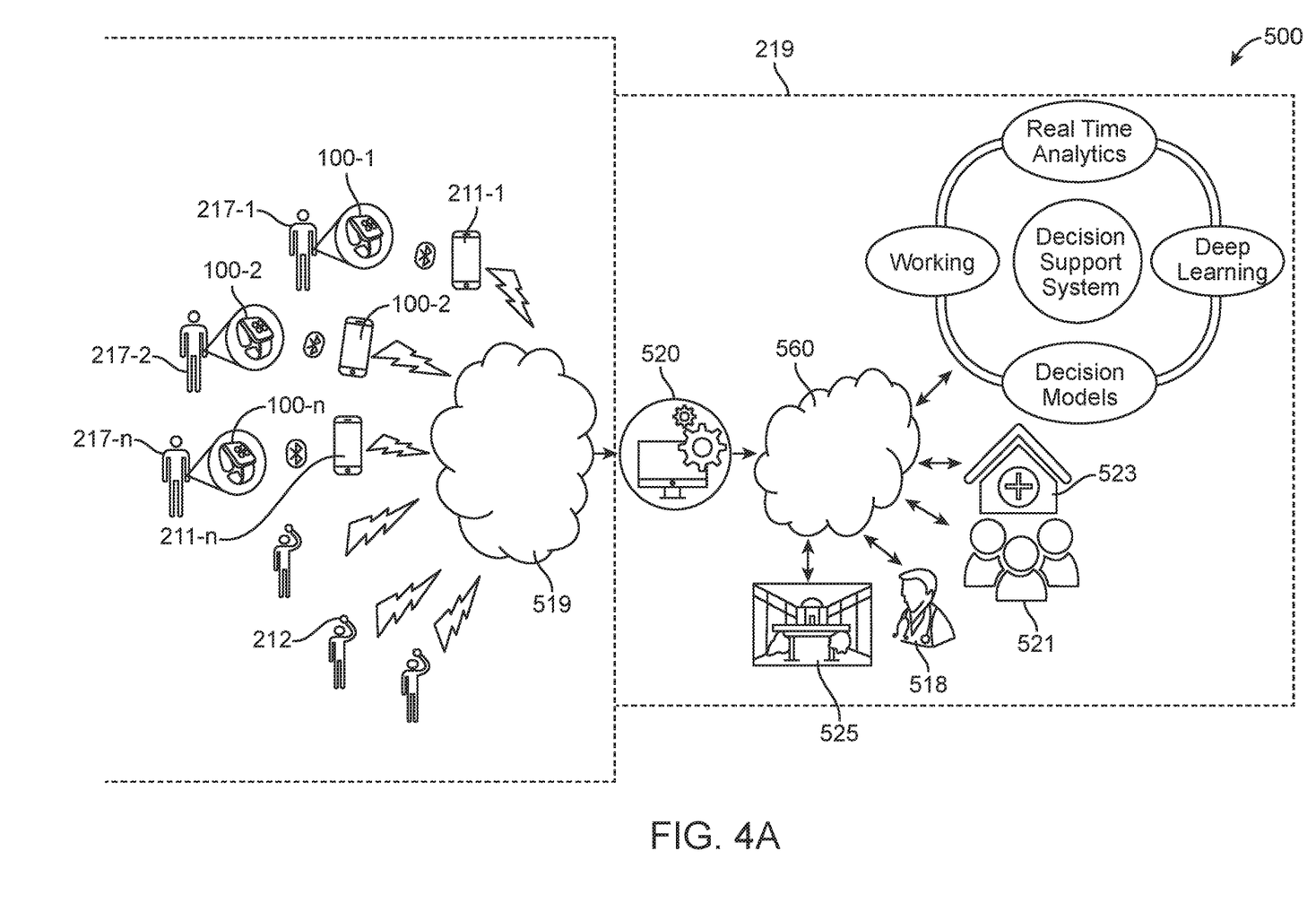
FIG. 4A illustrates the remote health monitoring system.

Referring now to FIG. 4A, a multi-parameter remote health monitoring system 500 is illustrated, according to embodiments of the invention. The health monitoring system 500 includes a plurality of user systems (i.e. individual IoT devices 100 coupled to corresponding smart devices 211 associated with unique users 217) connected to a remote computing device 219, such as a local or remote server, through a network 519. The server may include a central device 520 further interfaced to other systems and subsystems such one or more end devices 525, 518, 521, 523 via a hospital information system (HIS) 560. In some embodiments, the central device 520, user devices 211, end devices 525, 518, 521, 523 are communicatively coupled with the HIS 560 to form an integrated system. In other embodiments, they are external systems. The end device may connect in various embodiments to one or more of a clinic/hospital 523, a health care professional 518, a care giver 521 and a research institution 525 for research purposes.

In some embodiments the end device users may customize one or more parameters by including sensor reading patterns, medication, recovery activities, and instructions according to needs of their patients. In some embodiments the system may generate an alert signal when at least one of the monitored patient physiological parameters exceeds a set personalized sensor threshold. The information received at the HIS 560 is processed, compressed, stored and distributed to one or more other devices. In one embodiment this integration is performed in the cloud network which enables dynamic synchronization of results, notifications and updates from cloud server among patients and medical support systems.

Figure 4B:
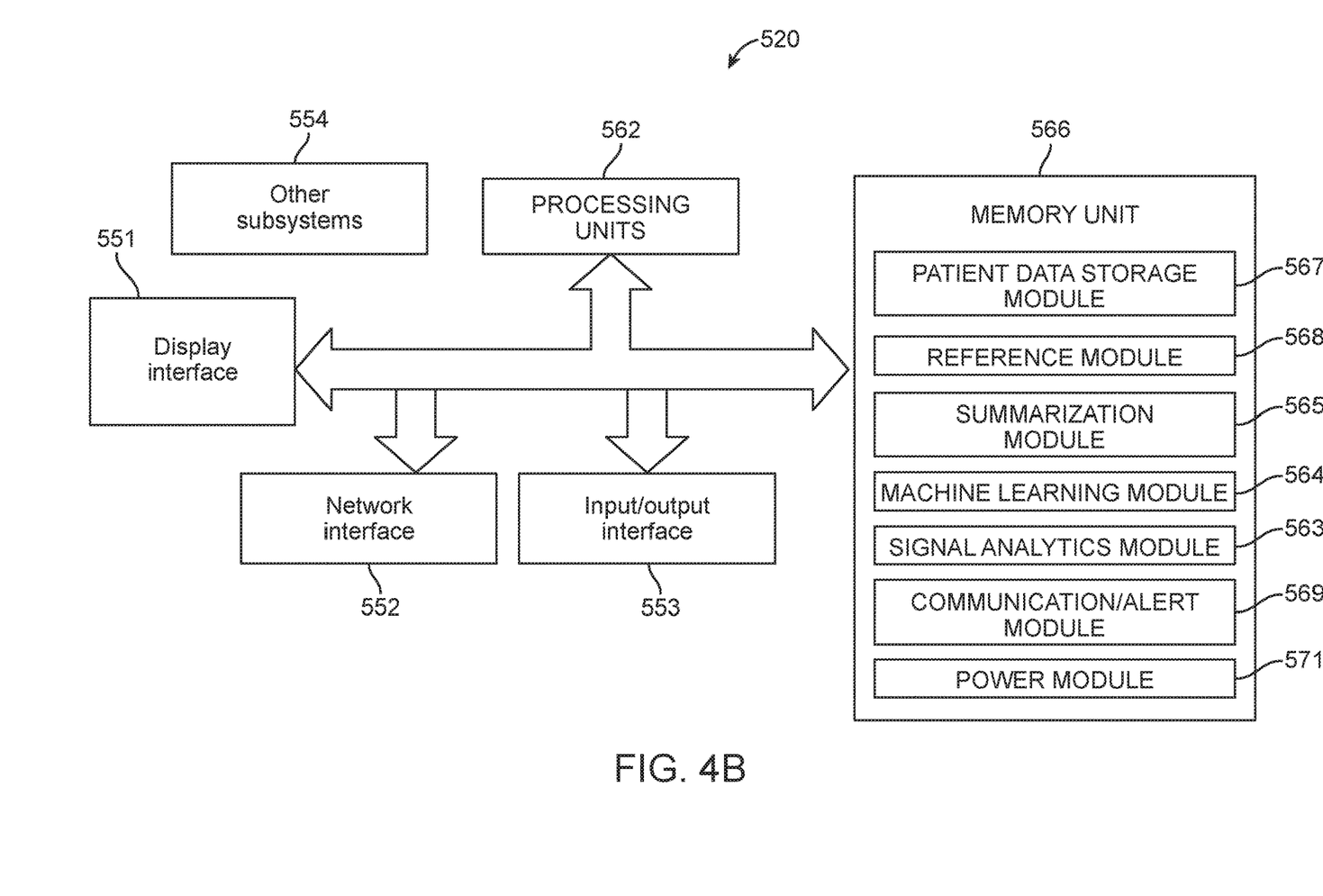
FIG. 4B shows the system architecture.

Referring now to FIG. 4B, a system architecture diagram is illustrated, according to embodiments of the invention. The system includes one or more of processing units 562, memory units 566 coupled to the one or more processing units, a display interface 551, a network interface 552, an input/output interface 553, and other sub systems 554. The memory unit includes various modules for performing the method as claimed herein. The system may access one or more data sources tied to the memory unit 566, or one or more additional systems such as the HIS 560 or the user device 211 via the network interface. Further, a communication or alert module 569 is configured to send alerts or signal data to the user device 211 or end devices 525, 518, 521, 523 via HIS 560. A power module 571 is configured to monitor and improve power utilization of various end devices under various circumstances.

A signal analytics module 563 is configured to receive sensor data of a patient from the wearable sensor device 100, apply one or more filters to remove motion artifacts, noise related interferences, effects of shivering, applied pressure, horizontal or vertical movements associated with the received sensor data, and extract a plurality of features from the PPG signal data. The plurality of features may comprise at least systolic duration, diastolic duration, systolic slope, diastolic slope, pulse duration, overall mean, peak amplitude, left half and right half of each PPG signal pulse. A machine learning module 564 is configured to predict or compute values for blood glucose, blood pressure, SpO2, respiration rate, pulse rate, or a combination thereof, from the extracted plurality of features, and further compute a threshold range for the patient based on at least one or more additional features including age, gender and disease status of the patient. An alert module 569 is configured to send an alert to one or more computing devices 518, 521, 523, 525, 211 when the values for blood glucose, blood pressure, SpO2, respiration rate, pulse rate, or a combination thereof, falls within or above the computed threshold range for the patient.

No alert may be raised if the value is below the predetermined threshold range for the patient. The alert module raises a moderate alert if the value falls within the computed threshold range. A severe alert is raised if the value falls above the threshold range. A summarization module 565 is configured to display a summary of the patient health status on the one or more computing device 518, 521, 523, 525, 211. The summarized parameters and/or other information related to one or more patients are placed in the patient data storage module 567 of the memory unit for secured distribution on a requirement basis. The memory unit may include a reference module 568 containing reference standards of each physiological parameter determined using conventional techniques. In some embodiments context-aware monitoring is also integrated with the signal analysis to capture the correlation between the multiple parameters and the relevant contexts with respect to available energy. In some embodiments, a signal quality module is configured to provide immediate feedback of the quality of received signal, to the patients to enable them to adjust alignment of wearable sensor device thereby enabling better signal transmission. In some embodiments quality assurance is performed in all networked devices and their performance to ensure the capture, analysis and transmission of high quality signals. In various embodiments the critical communications are prioritized based on the monitored signal strength and stability of the network.

In certain embodiments, smart devices 212 in the proximity of the patient devices 211, act as the edge and gateway nodes in the system 500. They do the functionalities of first level of sensor signal analysis, context aware monitoring, resilient communication, and context aware prioritization. In various embodiments the system monitors self-care, and collaborative treatment between different hospitals.

In some embodiments, the accuracy of the patient vitals obtained using the device, system and method as claimed herein is greater than 90% for pulse rate value measurements, greater than 90% for SpO2 value measurements, greater than 80% for blood pressure value measurements, and greater than 70% for blood glucose value measurements. In the various embodiments illustrated herein, the systems and methods of the invention present an easy, non-invasive way to obtain the accuracy of a clinical measurement of the health parameters of a patient using judicious correlation of non-invasive measurements and applying advanced predictive techniques to process the same.

The communication architecture enable continuous real-time monitoring of the patient from anywhere with internet connectivity, and thus provide up-to-date feedback about the status of the patient. This will further reduce the delay in treatment of the patient. The multi-parameter remote health monitoring system enables seamless information flow throughout the patient lifecycle, beginning right from the patient registration into the HIS system, distribution of the wearable sensor device, real-time data gathering, medical consultation, disease diagnosis, detection, treatment and post treatment stages.

EXAMPLES

Example 1: Fabrication of IoT Sensor Device

Figure 5:
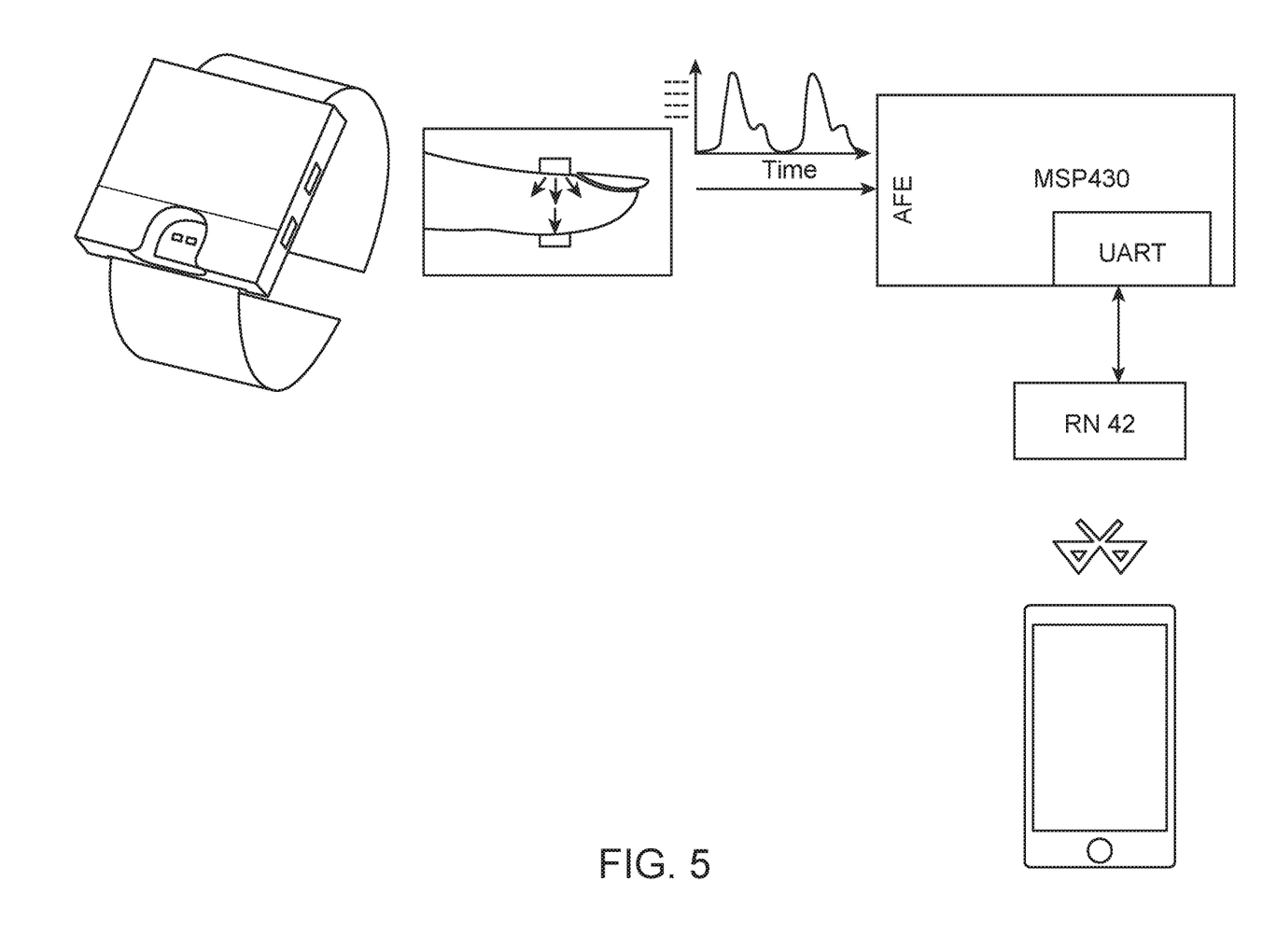
FIG. 5 shows an implementation of finger-worn IoT sensor device for sensing patient parameters using NIR spectroscopy.

With the goal of helping the burgeoning number of people with cardiovascular, diabetes lifestyle related and other non-communicable diseases, a prototype of the wearable device that uses an optical sensor to produce photo-plethysmograph (PPG) signal and machine learning techniques to measure non-invasively at least five body parameters such as blood pressure, respiratory rate, pulse rate, blood oxygen, and blood glucose, was developed. The implementation of the wearable watch IoT sensor device prototype is shown in FIG. 5. Validation of this system on more than 100 patients (from in hospital, remote clinics, and PHCs) showed that the maximum error rates were in the range of 7%-23% for blood glucose, 13%-15% for BP, and 10% for the SpO2 measurements which is much better than prior art devices and systems.

Example 2: System and Method Based on Predictive Models for Accurate Detection of PPG Signal Data For building up a proficient model for detecting anomalies using the PPG signal data of the device of Example 1, feature selection and extraction was done from a database containing medical data for a large number of subjects. For instance, the medical data included invasive, partially invasive or traditional approaches, such as cuff based blood pressure (BP) measurement data using a clinical device (sphygmomanometer) and invasive blood glucose (BG) measurements using a 'One touch glucometer' that uses the pin and prick method. Table 1 and 2 illustrates a limited sample dataset for BP and BG, respectively.

TABLE 1

SAMPLE DATASET DETAILS FOR BP

| BP Ranges | Systolic Band (mmHg) | Diastolic Band (mmHg) | Number of Subjects in Systolic band |
|---|---|---|---|
| Pre-hypertension BP | 120-140 | 80-90 | 41 |
| Low BP | <90 | <60 | 7 |
| Hypertension BP | >140 | >90 | 62 |
| Normal (Ideal) BP | 90-120 | 60-80 | 60 |

TABLE 2

SAMPLE DATA SET DETAILS FOR BG

| Condition | Band (mg/dL) | Number of Subjects |
|---|---|---|
| Fasting | 80-200 | 77 |
| Random | 100 and above | 64 |

The primary signal source for blood pressure and blood glucose estimation using wearable devices and systems of the present invention is from the non-invasively obtained PPG signal data from the wearable device. The IR LED PPG signal was used to derive a predictive model for BP analysis based on support vector regression (SVR) analysis. Once a subject places his/her finger on our device, the PPG wave was captured. The analog front end converts the captured signal into digital signal and is sent to the microcontroller-module for further processing. This signal is then transmitted wirelessly (using Bluetooth) to an android Mobile phone where further processing takes place.

The system was trained to detect anomalies from the PPG signal data using at least a Feature Extraction Algorithm and Support Vector Regression Algorithm for predicting Blood Pressure and Blood Glucose and mathematical models for the prediction of Pulse Rate, SpO2 and Respiration Rate, which were all embedded in an android app named 'Vitals Monitoring App'. The trained machine learning classifier predicted the vitals. Alerts were given to the user as well as sent to the doctor/physician, based on the results predicted. Based on preset calculations, the values are predicted for each of the physiological parameters.

In one example, in case of Fasting condition, if the blood glucose reading was shown between 100 and 125 mg/dL, the app generated a moderate alert for pre-diabetic condition and if the reading is greater than 126 mg/dL, the app showed a severe alert for diabetic condition. In another example, in case of 2-hour post-prandial glucose measurement, if the reading was between 140 and 199 mg/dL, the app showed a moderate alert for pre-diabetic condition and if the reading was greater than 200 mg/dL, the app showed a severe alert for diabetic condition. In yet another example, in case of random glucose measurements and there was no pre-diabetic condition but if the reading was greater than 200 mg/dl, the app showed a severe alert for diabetic condition. Similarly, for blood Pressure, hypotension, pre-hypertension and hypertension alerts were generated based on the readings. In one example, if the systolic BP level is below 90 mmHg, a low BP alert is generated. If the BP level was between 120 and 140 mmHg, then a pre-hypertension alert is generated and if the BP level was greater than 140 mmHg, then a severe hypertension alert is generated. If the diastolic BP level was below 60 mmHg, a low BP alert was generated. If the BP level is between 80 and 90 mmHg, then a pre-hypertension alert was generated and if the BP level is greater than 90 mmHg, then a severe hypertension alert was generated.

In case of SpO2, if the blood oxygen level is less than or equal to 92% a low blood oxygen level alert was generated. Pulse rate alerts were generated in two cases, one, if the heart rate is too low, i.e., below 60 bpm (beats per minute) and if the heart beats too fast, i.e., above 100 bpm. For Respiratory rate, the alerts were generated using the following condition. For an adult, a respiration rate under 12 or over 25 breaths per minute while resting is considered abnormal, and an alert is generated for this.

Figure 6A:
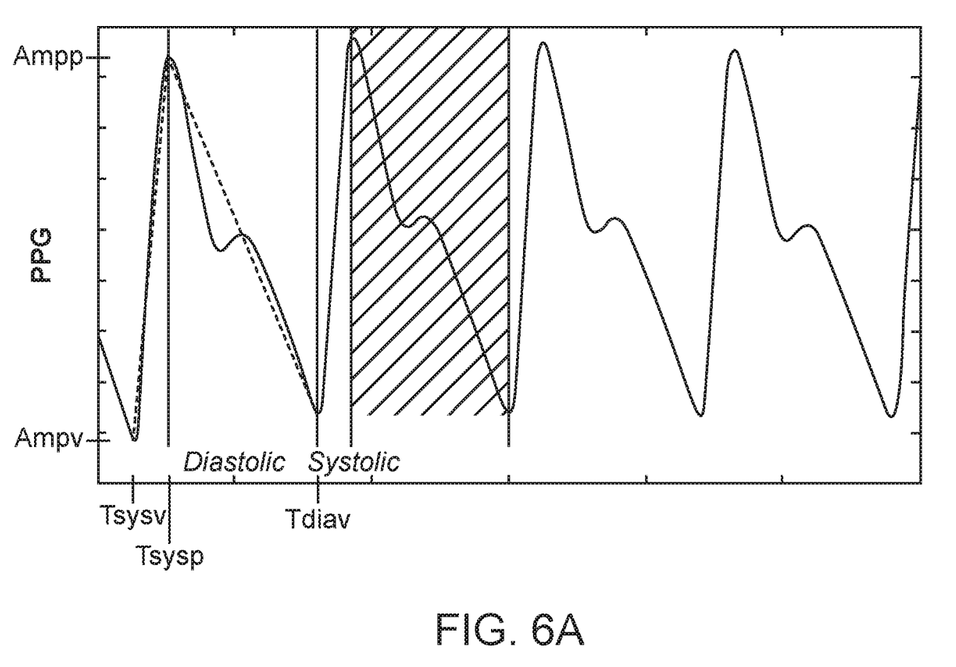
FIG. 6A shows extraction of features from PPG signal data.
Figure 6B:
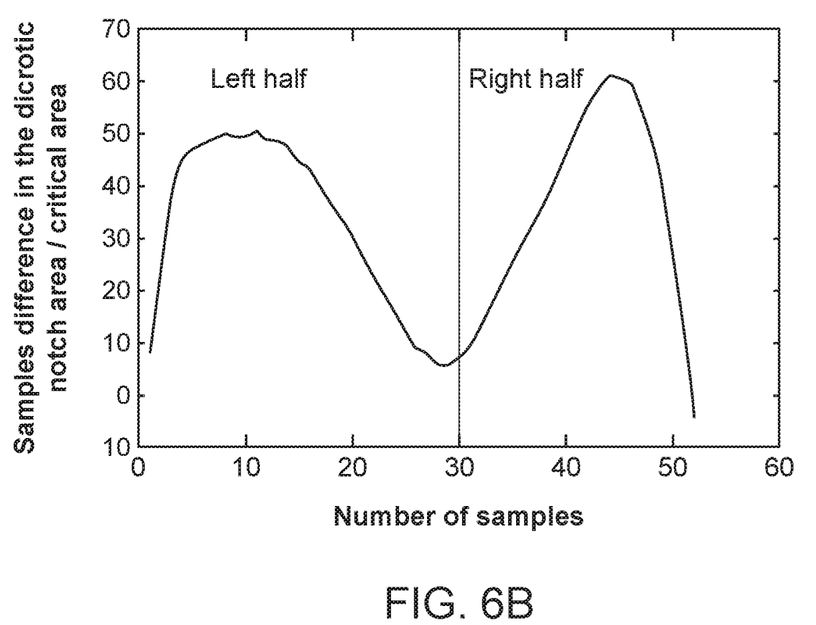
FIG. 6B shows extraction of left and right half features from dicrotic notch of PPG signal data.

In an exemplary implementation, we used 11 PPG features including: 1) Systolic duration—time interval between PPG valley point and next PPG peak point, 2) Diastolic duration—time interval between PPG peak point and next PPG valley point, 3) Systolic slope—defined as the slope of waveform in the systolic region, 4) Diastolic slope—defined as the slope of waveform in the diastolic region, 5) Pulse duration—studied along with features for generating the model for blood pressure, 6) Overall mean, 7) left half, 8) right half, 9) gender, 10) age, and 11) peak amplitude. A total of 170 subjects and four bands are considered for BP analysis. As illustrated in FIG. 6A, the region between PPG peak point and next PPG valley point (shaded region) vary from person to person as compared to the other region i.e., region between PPG valley point and next PPG peak point. Therefore this region (shaded region) can be used to derive more PPG features. The mean of the difference between adjacent samples in both left and right regions was calculated. From this, difference between adjacent samples in the shaded region, overall mean is calculated and was taken to derive model for BP and BG calculation. In PPG signal, dicrotic notch is a small, downward deflection observed on the downstroke of an arterial pressure waveform and represents closure of the aortic or pulmonic valve at the onset of ventricular diastole. It is a critical region as it varies from person to person. This measure was used to calculate the left and right half as shown in FIG. 6B.

Four bands includes: Hypertension (Hyp): above 140 mmHg, Pre Hypertension (Pre): 120-140 mmHg, Ideal: 90-120 mmHg, Low: below 90 mmHg. Before arriving at the model, we applied mean normal standardization on our dataset. As SVR adopts an ε-insensitive loss function, SVR input parameters, such as kernel function and epsilon are varied for improved and better output results. In order to analyse our method performance, we have used Mean Absolute Error (MAE) as shown in Table 3.

TABLE 3

MEAN ABSOLUTE ERROR (MAE) ANALYSIS FOR BP

| BP Ranges | MAE Systolic (mmHg) | MAE Diastolic (mmHg) | Systolic error % | Diastolic error % | Systolic STDEV (mmHg) | Diastolic STDEV (mmHg) |
|---|---|---|---|---|---|---|
| Normal (Ideal) BP | 5.23 | 5.6 | 4.980952381 | 8 | 6.75 | 6.38 |
| Prehypertension BP | 4.25 | 11.65 | 3.269230769 | 13.70588235 | 4.46 | 8.8 |
| Hypertension | 9.95 | 8.16 | 6.03030303 | 8.589473684 | 12.85 | 9.25 |
| Avg | 6.48 | 8.47 | 4.76 | 10.10 | 8.02 | 8.14 |
| Whole set* | 7.49 | 7.51 | | | 9.53 | 9.51 |

On acquiring the PPG signal from the sensor, the data from the IR channel was extracted to derive a predictive model for non-invasive blood glucose estimation. As mentioned in the above BP analysis, the same 11 PPG features were used for predicting blood glucose concentration, out of which left and right half means are unique features in case of BG. The model is obtained through SVR method for which 80% of data was kept for training and 20% for testing purpose. The analysis is made for different glucose ranges. The ranges were subdivided into: Range 1: —80-100 mg/dL; Range 2: —101-150 mg/dL; Range 3: —151-200 mg/dL and Range 4: —greater than 200 mg/dL; Range 5: —80-200 mg/dL and Range 6: —101 and above. Out of which reliable results are given below in Table 4 along with the corresponding ranges.

TABLE 4

MEAN ABSOLUTE ERROR (MAE) ANALYSIS FOR BG

| Band (mg/dL) | State (Fasting/Random) | Number of subjects | MAE (mg/dL) | % w.r.t. baseline |
|---|---|---|---|---|
| 80-200 | Fasting | 77 | 8.87 | 8.06 |
| 101 and above | Random | 64 | 30.49 | 21.78 |

The baseline used for determining the error percentage was decided by taking the median point in the respective band range. Additionally, pulse rate, SpO2 and respiration rate analysis was carried out using the PPG signal data. The results are shown in Table 5.

TABLE 5

PR, RR AND SPO2 ERROR ANALYSIS

| Parameter | No. of subjects | Error % |
|---|---|---|
| Pulse Rate (PR) | 55 | 7 |
| SpO2 | 55 | 3 |
| Respiration Rate (RR) | 25 | 7 |

Figure 7:
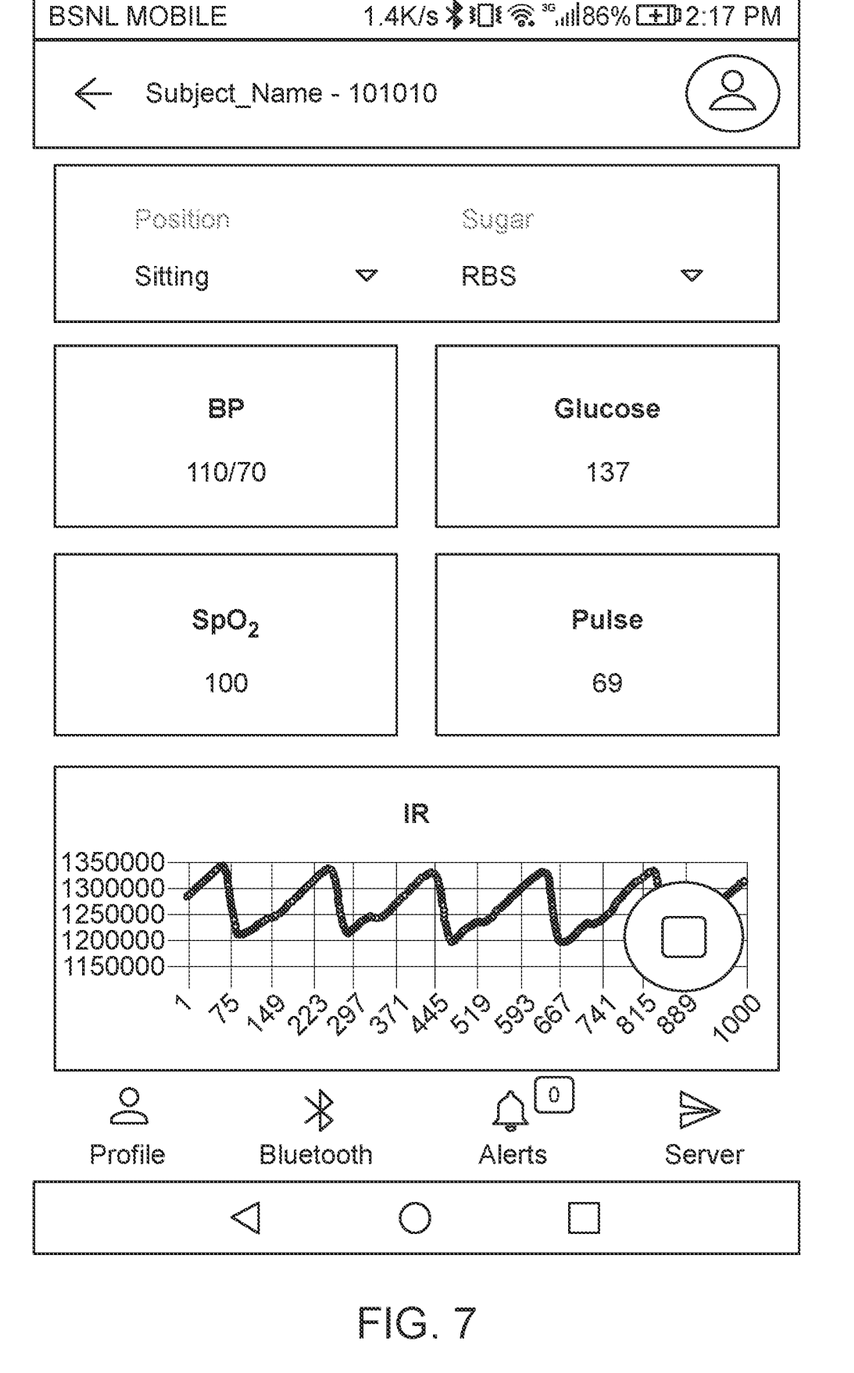
FIG. 7 shows a screenshot of a smartphone running the vitals monitor application.

A screenshot of a sample output of the results that may be presented to one or more users through a smartphone is shown in FIG. 7. The graphical user interface of the application enables actionable insights for the subjects being monitored.

Although the detailed description contains many specifics, these should not be construed as limiting the scope of the invention but merely as illustrating different examples and aspects of the invention. It should be appreciated that the scope of the invention includes other embodiments not discussed herein. Various other modifications, changes and variations which will be apparent to those skilled in the art may be made in the arrangement, operation and details of the system and method of the present invention disclosed herein without departing from the spirit and scope of the invention as described here. While the invention has been disclosed with reference to certain embodiments, it will be understood by those skilled in the art that various changes may be made and equivalents may be substituted without departing from the scope of the invention.

What is claimed is:

1. A method, comprising:
mounting a wearable sensor device to a position on a specific subject, the wearable sensor device comprising a microcontroller, transceiver circuitry enabled to communicate wirelessly, an optical emitter, and an optical sensor;
determining a physiological signal from the subject by interaction of the optical emitter and the optical sensor;
transmitting the physiological signal wirelessly to a nearby computerized appliance enabled to connect to the Internet network;
connecting the computerized appliance to an Internet-connected server;
transmitting the physiological signal to the Internet-connected server along with identification of the specific subject;
extracting, by software executing on a processor of the Internet-connected server, a plurality of features from the physiological signal, the plurality of features comprising at least systolic duration, diastolic duration, systolic slope, diastolic slope, pulse duration, overall mean, and peak amplitude;
providing the plurality of features to a machine-learning module trained to predict values for blood glucose, blood pressure, SpO2, respiration rate, and pulse rate;
predicting values for blood glucose, blood pressure, SpO2, respiration rate, and pulse rate for the specific subject by the machine-learning module;
computing a threshold range for blood glucose, blood pressure, SpO2, respiration rate, and pulse rate by the machine-learning module, based on stored vales of age, gender and disease status of the specific subject; and
issuing an alert by an alert module to one or more persons when and if a value for the physiological parameter for the specific subject is determined to be out of the threshold range.

2. The method of claim 1 wherein the nearby computerized appliance is a Smartphone, further comprising the smartphone connecting to the Internet-connected server and transmitting the physiological signal.

3. A system, comprising:
a wearable sensor device mounted to a position on a specific subject, the wearable sensor device comprising a microcontroller, transceiver circuitry enabled to communicate wirelessly, an optical emitter, and an optical sensor;
a nearby computerized appliance enabled to connect to the Internet network receiving wirelessly a physiological signal from the wearable sensor device, the physiological signal determined by interaction of the optical emitter and the optical sensor;
an Internet-connected server coupled to a memory unit storing historical data for the specific subject and executing software;
wherein the nearby computerized appliance receives the physiological signal from the wearable sensor device along with identification of the specific subject, connects to the Internet-connected server, and transmits the physiological signal to the Internet-connected server along with the identification of the specific subject, and wherein the Internet-connected server extracts a plurality of features from the physiological signal, the plurality of features comprising at least systolic duration, diastolic duration, systolic slope, diastolic slope, pulse duration, overall mean, and peak amplitude, provides the plurality of features to a machine-learning module trained to predict values for blood glucose, blood pressure, SpO2, respiration rate, and pulse rate, the machine-learning module computes a threshold range for blood glucose, blood pressure, SpO2, respiration rate, and pulse rate for the specific subject, based on stored values of age, gender and disease status of the specific subject, and issues an alert by an alert module to one or more persons when and if the value for the physiological parameter for the specific subject is determined to be outside the threshold range.

4. The system of claim 3 wherein the nearby computerized appliance is a Smartphone, comprising the smartphone connecting to the Internet-connected server and transmitting the physiological signal.

* * * * *